United States Patent [19]

Schmidt

[11] 3,956,427
[45] May 11, 1976

[54] BENZYLATED PHOSPHORIC ACID HYDRAZIDES

[75] Inventor: Andreas Schmidt, Reinach, Switzerland

[73] Assignee: Ciba-Geigy Corporation, Ardsley, N.Y.

[22] Filed: Oct. 21, 1974

[21] Appl. No.: 516,228

[30] Foreign Application Priority Data
Oct. 31, 1973 Switzerland.................. 15329/73

[52] U.S. Cl................. 260/923; 252/46.7; 252/51; 260/45.95 L; 260/398.5; 260/455 A
[51] Int. Cl.² .................. C07F 9/12; C08K 5/53
[58] Field of Search ............................. 260/923

[56] References Cited
UNITED STATES PATENTS

| | | | |
|---|---|---|---|
| 2,906,770 | 9/1959 | Debo | 260/923 |
| 3,355,521 | 11/1967 | Bliss et al | 200/923 |

Primary Examiner—Anton H. Sutto
Attorney, Agent, or Firm—Charles W. Vanecek

[57] ABSTRACT

New benzylated phosphoric acid hydrazides are stabilisers for organic material. They are manufactured from corresponding benzyl hydrazides and phosphoric acid monochlorides or thiophosphoric acid monochlorides.

4 Claims, No Drawings

BENZYLATED PHOSPHORIC ACID HYDRAZIDES

The invention relates to new benzylated phosphoric acid hydrazides, a process for their manufacture, their use for the protection of organic material which is sensitive to oxidation and to light, and, as an industrial product, the organic material protected with their aid.

The new compounds correspond to the general formula I

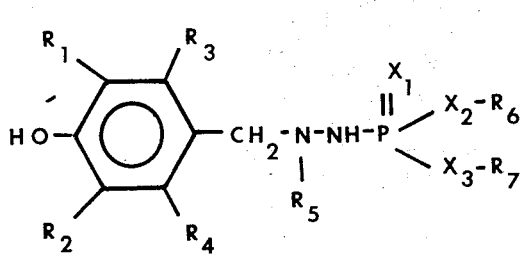

(I)

in which $R_1$ denotes alkyl, cycloalkyl or aralkyl, $R_2$ denotes hydrogen, alkyl, cycloalkyl or aralkyl, $R_3$ and $R_4$ independently of one another denote hydrogen or lower alkyl, $R_5$ denotes hydrogen or one of the groups

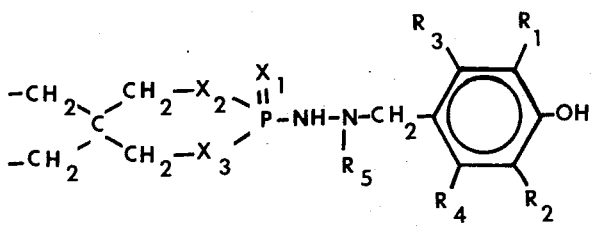

$R_6$ and $R_7$ independently of one another denote alkyl, alkenyl, cycloalkyl, aralkyl or aryl, or $R_6$ and $R_7$ conjointly denote 1,2-alkylene, 1,3-alkylene, o-arylene or 1,8-naphthylene, or, if $R_5$ denotes a phosphorus-free group, also denote a group

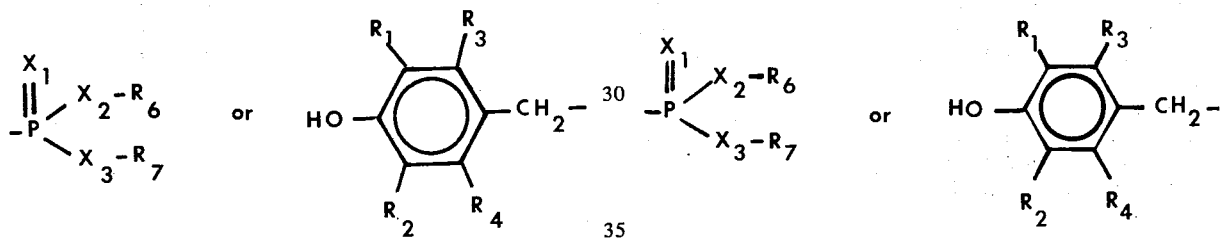

and $X_1$, $X_2$ and $X_3$ independently of one another denote oxygen and/or sulphur, not more than 2 radicals out of $X_1$, $X_2$ and $X_3$ being sulphur.

The use of phosphorus compounds for stabilising organic material against thermo-oxidative damage is known. Amongst these compounds those which are reducing agents are widely used; phosphites, such as are described, for example, in "Stabilisierung der Kunststoffe gegen Licht und Waerme ("Stabilisation of Plastics against Light and Heat"), Joachim Voigt, Springer Verlag, Volume I, 1966, page 326," are most widely used. As a result of their sensitivity to hydrolysis, however, these cause two decisive disadvantages. Firstly, the compounds are not stable on storage, and, secondly, as a result of the hydrolysis, acid cleavage products are formed which can harm the material to be stabilised.

On the other hand, phosphates, such as are described for example, in "Stabilisierung der Kunststoffe gegen Licht und Waerme ("Stabilisation of Plastics against Light and Heat"), Joachim Voigt, Springer Verlag, Volume I, 1966, page 328," are compounds which are distinguished by good stability towards hydrolysis, but their effectiveness as stabilisers is inadequate and often non-existent.

The use of hydrazine derivatives of phenols as stabilisers for organic material is also known.

It has now been found, surprisingly, that the new, benzylated phosphoric acid hydrazides of the formula I are better anti-oxidants against thermo-oxidative degredation than the previously known hydrazine derivatives of sterically hindered phenols, do not exhibit the disadvantages described of effective phosphorus compounds, and, in addition, give protection against damage caused by light, such as UV light. Preferred compounds are those of the formula I in which $R_1$ denotes alkyl having 1–8 carbon atoms, cycloalkyl having 6–8 carbon atoms, or aralkyl having 7–9 carbon atoms, $R_2$ denotes hydrogen, alkyl having 1–8 carbon atoms, cycloalkyl having 6–8 carbon atoms, or aralkyl having 7–9 carbon atoms, $R_3$ and $R_4$ independently of one another denote hydrogen or methyl, $R_5$ denotes hydrogen or one of the groups $R_6$ and $R_7$ independently of one another denote alkyl having 1–22 carbon atoms, cycloalkyl having 5–8 carbon atoms, halogenoalkyl having 2–18 carbon atoms, thiaalkyl having 3–21 carbon atoms, wherein $X_2$ and $X_3$ are linked to a carbon atom in the thiaalkyl radical which does not carry other hetero-atoms, oxaalkyl having 3–21 carbon atoms, wherein $X_2$ and $X_3$ are linked to a carbon atom in the oxaalkyl radical which does not carry other hetero-atoms, alkenyl having 3–4 carbon atoms, aralkyl having 7–15 carbon atoms, phenyl, alkylphenyl having 7–14 carbon atoms, alkoxyphenyl having 7–14 carbon atoms, chlorophenyl or phenylphenyl, or $R_6$ and $R_7$ conjointly denote 1,2-or 1,3-alkylene having 2 to 8 carbon atoms, or o-phenylene or, if $R_5$ denotes a phosphorus-free group, also a group

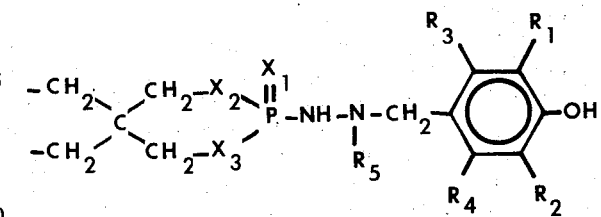

and $X_1$, $X_2$ and $X_3$ independently of one another denote oxygen and/or sulphur, not more than 2 radicals out of $X_1$, $X_2$ and $X_3$ being sulphur.

Particularly preferred compounds are those of the formula I in which $R_1$ denotes alkyl having 1–4 carbon atoms, such as tert.butyl, $R_2$ denotes alkyl having 3 or 4 carbon atoms, such as tert.butyl, $R_3$ and $R_4$ denote hydrogen, $R_5$ denotes hydrogen or a group

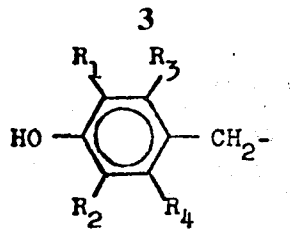

$R_6$ and $R_7$ independently of one another denote alkyl having 1–8 carbon atoms, benzyl, phenyl or alkylphenyl having 7–14 carbon atoms, or $R_6$ and $R_7$ conjointly denote ethylene, 1-methyltrimethylene, 2,2-dimethyltrimethylene, o-phenylene or a group

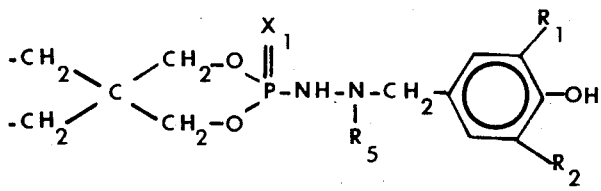

$X_1$ denotes oxygen or sulphur, and $X_2$ and $X_3$ denote oxygen.

In the definition of the compounds of the formula I, it is possible for $R_1$, $R_2$, $R_6$ and/or $R_7$ to be alkyl groups.

They can, for example, be methyl, ethyl, iso-propyl, n-butyl, sec.-butyl, tert.-butyl, n-amyl, tert.-amyl, sec.-amyl, hexyl, octyl, tert.-octyl, decyl, dodecyl, tetradecyl or octadecyl.

$R_3$ and/or $R_4$ can be lower alkyl, preferably having 1 to 4 carbon atoms, such as methyl, ethyl, iso-propyl, n-butyl, sec.-butyl or tert.-butyl.

$R_1$, $R_2$, $R_6$ and/or $R_7$ can also denote cycloalkyl groups, such as cyclopentyl, cyclohexyl, α-methylcyclohexyl or cyclooctyl.

$R_1$, $R_2$, $R_6$ and/or $R_7$ can also be aralkyl groups, such as benzyl, α-phenylethyl or α,α-dimethylbenzyl.

$R_6$ and/or $R_7$ can be unsubstituted alkyl groups, as in the examples given above. They can, however, also be substituted alkyl groups, such as oxaalkyl, thiaalkl or halogenoalkyl.

In the meaning of oxaalkyl, $R_6$ and/or $R_7$ can be, for example, 3-oxabutyl, 3-oxapentyl, 3-oxaheptyl, 3-oxapentadecyl or 3-oxaheneicosyl, and, in the meaning of thiaalkyl, they can be, for example, 3-thiabutyl, 3-thiapentyl, 3-thiaheptyl, 3-thiaundecyl, 3-thiapentadecyl, 3-thianonadecyl and 3-thiaheneicosyl.

$R_6$ and/or $R_7$ can also be halogenoalkyl, preferably chloroalkyl, such as —$CH_2CH_2Cl$ or —$CH_2CH_2$—$CHCl$—$CH_3$.

In the meaning of alkenyl, $R_6$ and/or $R_7$ can be propenyl.

If $R_6$ and/or $R_7$ denote aryl, they can be an unsubstituted phenyl or naphthyl radical. The radicals can, however, also be substituted by alkyl, such as methyl, ethyl, propyl, n-butyl, sec.-butyl or tert.-butyl; alkoxy, such as methoxy, ethoxy, propoxy or n-butoxy; halogen, such as chlorine or bromine; or phenyl.

Examples of such substituents are 2-isopropyl-5-methylphenyl, 4-tert.butylphenyl, 4-phenylphenyl, 2-chlorophenyl, 4-chlorophenyl and 2-methoxyphenyl.

$R_6$ and $R_7$ can conjointly be 1,2-alkylene or 1,3-alkylene, such as, for example, propylene, 1-methyltrimethylene, 2,2-dimethyltrimethylene, 1,3-dimethyltrimethylene, 1-propyl-2-ethyltrimethylene and 2-phenyltrimethylene, or o-arylene, such as o-phenylene.

Examples of compounds of the formula I are: N(3-tert.butyl-4-hydroxy-5-methylbenzyl)-thiophosphoric acid O,O-diethyl ester hydrazide, N(3,5-ditert.butyl-4-hydroxybenzyl) phosphoric acid diethyl ester hydrazide, N,N-bis(3-tert.butyl-4-hydroxy-5-methylbenzyl)-thiophosphoric acid O,O-diethyl ester hydrazide, N(3,5-ditert.butyl-4-hydroxybenzyl)thiophosphoric acid O,S-diethyl ester hydrazide, N(2,3-dimethyl-4-hydroxy-5-tert.butylbenzyl)thiophosphoric acid O,O-diethyl ester hydrazide, N(2,3,6-trimethyl-4-hydroxy-5-tert.butylbenzyl)-thiophosphoric acid O,O-diethyl ester hydrazide, N[3,5-di(α-methylbenzyl)-4-hydroxybenzyl]thiophosphoric acid O,O-diethyl ester hydrazide, N[3,5-di(1-methylcyclohexyl)-4-hydroxybenzyl]-thiphosphoric acid O,O-diethyl ester hydrazide, N(3,5-ditert.pentyl-4-hydroxybenzyl)thiophosphoric acid O,O-diethyl ester hydrazide, N(3,5-di-isopropyl-4-hydroxybenzyl)thiophosphoric acid O,O-diethyl ester hydrazide, N(3,5-disec.butyl-4-hydrobenzyl)thiophosphoric acid O,O-diethyl ester hydrazide, N,N-bis(2,3-dimethyl-4-hydroxy-5-tert.butylbenzyl)phosphoric acid diethyl ester hydrazide, N(3,5-ditert.butyl-4-hydroxybenzyl)phosphoric acid dimethyl ester hydrazide, N(3,5-ditert.butyl-4-hydroxybenzyl)thiophosphoric acid O,O-o-phenylene ester hydrazide, N(3,5-ditert. butyl-4-hydroxybenzyl)thiophosphoric acid O,O-dioctadecyl ester hydrazide, N(3,5-ditert.butyl-4-hydroxybenzyl)dithiophosphoric acid O,S-diethyl ester hydrazide, N(3,5-ditert.-butyl-4-hydroxybenzyl)dithiophosphoric acid S,S-diethyl ester hydrazide, N,N-bis(3,5-ditert.butyl-4-hydroxybenzyl)-phosphoric acid dibenzyl ester hydrazide, N(3,5-ditert.butyl-4-hydroxybenzyl)phosphoric acid diphenyl ester hydrazide, N(3,5-ditert.butyl-4-hydroxybenzyl)phosphoric acid dibutyl ester hydrazide, N(3,5-ditert.butyl-4-hydroxybenzyl)phosphoric acid ethylene ester hydrazide, N(3,5-ditert.butyl-4-hydroxybenzyl)phosphoric acid di(p-tert.butylphenyl)ester hydrazide, N,N'-bis-diethoxythiophosphoryl-N-(3-tert.butyl-4-hydroxy-5methylbenzyl)-hydrazine and 3,9-bis-(3,5-ditert.-butyl-4-hydroxybenzylhydrazino)-2,4,8,10-tetraoxa-3,9-diphosphasiro[5,5]undecane-3,9-dioxide.

The compounds of the formula I in which $R_5$ denotes hydrogen or a group

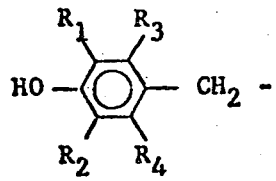

are prepared by reacting one molar equivalent of a compound of the formula II

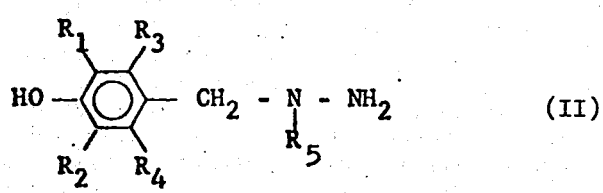

wherein $R_5$ denotes hydrogen or a group

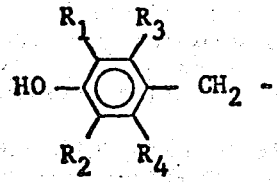

with one molar equivalent of a compound of the general formula III

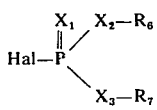 (III)

wherein "Hal" denotes chlorine, bromine or iodine, preferably chlorine, and the symbols $X_1$, $X_2$, $X_3$, $R_6$ and $R_7$ denote what is defined under formula I, in the presence of a base in order to neutralise the hydrogen halide formed. Those compounds of the formula I in which $R_5$ denotes hydrogen or a group

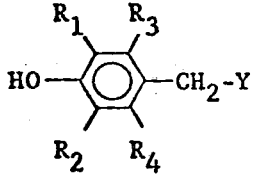

and $R_5$ and $R_7$ conjointly denote a group

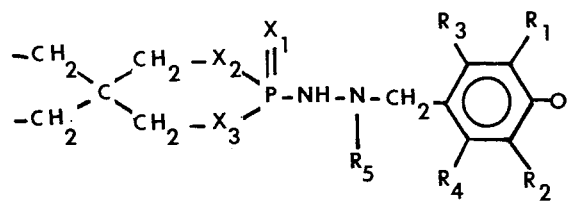

are advantageously prepared by reacting 2 molar equivalents of a compound of the formula II, having the above meaning for $R_5$, with one molar equivalent of a compound of the formula IIIa

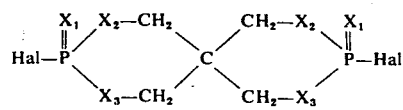 (IIIa)

The reaction is carried out in an aprotic, polar solvent, such as dioxane, dimethylformamide, dimethylacetamide, ethylene glycol dimethyl ether, tetrahydrofurane or acetone. The bases used are preferably tertiary amines such as pyridine, triethylamine, triisopropylamine and the like. The tertiary amines can advantageously be used directly as the solvent.

The compounds of the formula I in which $R_5$ denotes a group

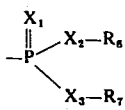

are prepared by reacting one molar equivalent of a compound of the formula II

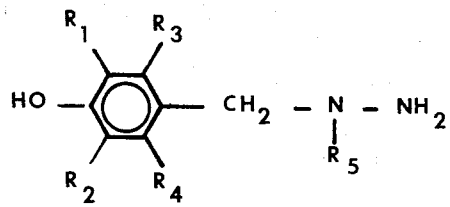 (II)

wherein $R_5$ denotes hydrogen, with 2 molar equivalents of a compound of the formula III. The reaction is carried out under conditions identical to those of the preceding reaction.

An alternative process for preparing the compounds of the formula I consists of reacting one or two molar equivalents of a compound of the formula IV

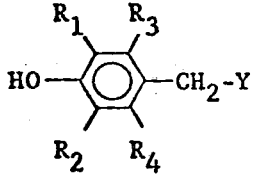 (IV)

wherein $R_1$, $R_2$, $R_3$ and $R_4$ have the meaning indicated under formula I, and Y denotes a halogen atom or one of the radicals

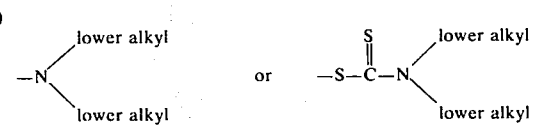

with one molar equivalent of a compound of the formula V.

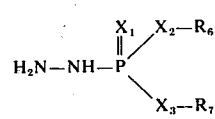 (V)

The reaction is preferably carried out in the presence of a basic catalyst, such as NaH, CaH$_2$, NaNH$_2$, LiNH$_2$, NaOCH$_3$ or the like, in a solvent such as isopropanol, tert.butanol, dioxane, tetrahydrofurane, benzene, toluene or ligroin.

The starting products of the formulae II, III, IIIa, IV and V are known or can be prepared easily by generally known methods.

The following are examples of substrates which can be used for the compounds of the formula I:

1. Polymers which are derived from hydrocarbons with single or double unsaturation, such as polyolefines, for example polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the monopolymers mentioned are based, such as ethylene-propylene copolymers, propylenebutene-1 copolymers, propylene-isobutylene copolymers, styrenebutadiene copolymers and terpolymers of ethylene and propylene with a diene, such as, for example, hexadine, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, and polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as a comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerol-phthalic acids resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. Natural and synthetic organic substances which are pure monomeric compounds or mixtures thereof, for example mineral oils, animal and vegetable fats, oils and waxes, or oils, waxes and fats based on synthetic esters and mixtures of synthetic esters with mineral oils in any desired weight ratios.

The compounds of the formula I are incorporated into the substrates in a cooncentration of 0.005 to 5% by weight calculated relative to the material to be stabilised.

Preferably, 0.01 to 1.0, and particularly preferentially 0.02 to 0.5, % by weight of the compounds, calculated relative to the material to be stabilised, are incorporated into the latter. The incorporation can take place for example by mixing in at least one of the compounds of the formula I and optionally further additives according to the methods customary in the art, before or during shaping, or by applying the dissolved or dispersed compounds to the polymer, if appropriate with subsequent evaporation of the solvent.

In the case of crosslinked polyethylene, the compounds are added before crosslinking.

The compounds of the formula I can also be added before or during the polymerisation and stabilised substrates in which the stabilisers are not volatile or extractable can be obtained through possible incorporation into the polymer chain.

As examples of further additives together with which the stabilisers can be employed, there should be mentioned:

1. Antioxidants 1.1 Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

1.2 Derivatives of alkylated hydroquinones, such as, for example, 2,5-di-tert.butyl-hydroquinone, 2,5-di-tert.amyl-hydroquinone, 2,6-di-tert.butyl-hydroquinone, 2,5-di-tert.butyl-4-hydroxy-anisole, 3,5-di-tert.butyl-4-hydroxy-anisole, tris-(3,5-di-tert.butyl-4-hydroxyphenyl) phosphite, 3,5-di-tert.butyl-4-hydroxyphenol stearate and bis-(3,5-di-tert.butyl-4-hydroxyphenol) adipate.

1.3 Hydroylated thiodiphenyl ethers, such as, for example 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol), 4,4'-thio-bis-(6-tert.butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2'-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5,-tetra-(5-tert.butyl-4-hydroxy-2-methylphenyl)-pentane and ethylene glycol bis-[3,3-bis-(3'-tert.butyl-4'-hydroxyphenyl)-butyrate].

1,5 O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)dithiol terephthalate.

1.6 Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didodecylmercaptoethyl ester and 2,2-bis-(3,5-di-tert.butyl-4-hydroxybenzyl) malonic acid di-[4-(1,1,3,3-tetramethylbutyl)-phenyl] ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as for exaample, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]-octane.

1.11 Esters of β-(5-tert.butyl-4-hydroxy-3-methylphenyl)-propionic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol,, 3-thiapentadecanol, trimethylhexanediol, trimethylolethane, trimethylolpropane, trishydroxyethylisocyanurate and 4-hydroxymethyl-1-phospha-2,6,7-trioxabicyclo[2,2,2]-octane.

1.12 Esters of 3,5-di-tert.butyl-4-hydroxyphenylacetic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.13 Acylaminophenols, such as, for example, N-(3,5-di-tert.butyl-4-hydroxyphenyl)-stearic acid amide and N,N'-di-(3,5-ditert.butyl-4-hydroxyphenyl)-thiobis-acetamide.

1.14 Benzylphosphonates, such as, for example 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert-.butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-1-naphthyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline.

2. UV absorbers and light stabilisers 2.1 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl- and 6-undecyl-derivative.

2.3 2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivative.

2.4 1,3-Bis-(2'-hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxybenzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester or octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxyvinyl)-2-methyl-indoline.

2.7. Nickel compounds, such as, for example, nickel complexes of 2,2'-thio-bis-[4-(1,1,3,3-tetramethyl-butyl)-phenol], such as the 1:1 or 1:2 complex, optionally with additional ligands such as n-butylamine, triethanolamine or N-cyclohexyldiethanolamine, nickel complexes of bis-[2-hydroxy-4-(1,1,3,3-tetramethyl-butyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzylphosphonic acid monalkyl esters such as of the methyl, ethyl, or butyl ester, nickel complexes of ketoximes, such as of 2-hydroxy-4-methyl-phenyl-undecylketonoxime, and nickel 3,5-di-tert.butyl-4-hydroxybenzoate.

2.8. Sterically hindered amines, such as, for example, 4-benzoyloxy-2,2,6,6-tetramethylpiperidine, 4-stearoyloxy-2,2,6-6-tetramethylpiperidine, bis-(2,2,6,6-tetramethylpiperidyl) sebacate and 3-n-octyl-7,7,9,9-tetramethyl-1,3,8-triazaspiro[4,5]decane-2,4-dione.

2.9 Oxalic acid diamides, such as, for example, 4,4'-dioctylocy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

3. Metal deactivators, such as, for example, oxanilide, isophthalic acid dihydrazide, sebacic acid bisphenyl-hydrazide, bis-benzylidene-oxalic acid dihydrazide, N,N'-diacetyl-adipic acid dihydrazide, N,N'-bis-salicyloyl-oxalic acid dihydrazide, N,N'-bis-salicyloyl-hydrazine, N,N'-bis-(3,5-di-tert.butyl-4-hydroxyphenyl-propionyl)-hydrazine, N-salicylal-N'-salicylidene-hydrazine and 3-salicyloylamino-1,2,4-triazole.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetroxa-3,9-diphospha-spiro[5,5]-undecane and tri-(4-hydroxy-3,5-di-tert.butylphenyl) phosphite.

5. Compounds which destroy peroxide, such as, for example, esters of β-thiodipropionic acid, for example the lauryl, stearyl, myristyl or tridecyl esters, salts of 2-mercaptobenzimidazole, for example the Zn salt, and diphenylthiourea.

6. Polyamide stabilisers, such as, for example, copper salts in combination with iodides and/or phosphorus compounds and salts of divalent manganese.

7. Basic co-stabilisers, such as, for example, malamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

8. PVC stabilisers, such as, for example, organic tin compounds, organic lead compounds and barium-cadmium salts of fatty acids.

9. Nucleating agents, such as, for example, 4-tert.-butyl-benzoic acid, adipic acid and diphenylacetic acid.

10. Other additives, such as, for example, plasticisers, lubricants, emulsifiers, fillers, carbon black, asbestos, kaolin, talc, glass fibres, pigments, optical brighteners, flameproofing agents and antistatic agents.

The manufacture and use of the compounds according to the invention is described in more detail in the examples which follow. Parts therein denote parts by weight.

EXAMPLE 1

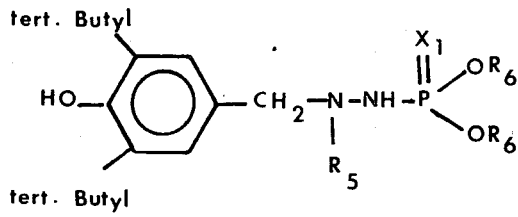

25.0 g (0.1 mol) of 3,5-ditert.butyl-4-hydroxybenzyl-hydrazine are initially placed in 100 ml of dry pyridine. 18.8 g (0.1 mol) of thiophosphoric acid O,O-diethyl ester chloride is added dropwise to the solution at room temperature. The mixture changes colour, from green to yellow, with gentle evolution of heat. The solution is diluted with 250 ml of toluene and is then extracted with several portions of dilute hydrochloric acid. After washing the mixture until it is neutral, drying and evaporating, an oil remains, which is worked up by column chromatography. N(3,5-Di-tert.butyl-4-hydroxybenzyl)-thiophosphoric acid O,O-diethyl ester hydrazide, having a melting point of 59°C (Stabiliser No. 1), is obtained in this way as a pure main fraction. The product can be recrystallised from petroleum ether.

If, in this example, a double quantity (37.6 g = 0.2 mol) of thiophosphoric acid O,O-diethyl ester chloride is used, N,N'-bis-diethoxythiophosphoryl-N-(3,5-ditert.butyl-4-hydroxybenzyl)-hydrazine, having a melting point of 103°C, (Stabiliser No. 2) is obtained under the same conditions as the main product. The product is recrystallised from hexane.

EXAMPLE 2

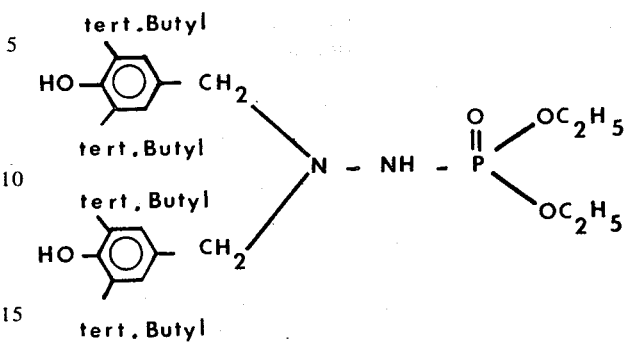

46.9 g (0.1 mol) of N,N-bis(3,5-ditert.butyl-4-hydroxybenzyl)-hydrazine are dissolved in 200 ml of pyridine. 17.2 g of diethylchlorophosphate are added dropwise to the solution at room temperature. The mixture is allowed to stand for some hours and is then evaporated. The residue is dissolved in toluene and the toluene solution is extracted with dilute hydrochloric acid and then with water. After evaporation, a yellowish oil remains, which crystallises slowly. N,N-Bis(3,5-ditert.butyl-4-hydroxybenzyl)-phosphoric acid diethyl ester hydrazide, having a melting point of 153°C, (Stabiliser No. 3) is obtained after recrystallisation from hexane.

If, in this example, the N,N-bis(3,5-ditert.butyl-4-hydroxybenyl)-hydrazine is replaced by an equivalent quantity of N,N-bis(3-tert.butyl-4-hydroxy-5-methylbenzyl)-hydrazine, an otherwise identical procedure gives N,N-bis-(3-tert.butyl-4-hydroxy-5-methylbenzyl)phosphoric acid diethyl ester hydrazide, having a melting point of 156°C. The product is recrystallised from acetonitrile (Stabiliser No. 4).

EXAMPLE 3

Stabilisation of polypropylene against degradation during processing 0.1 part of Stabiliser No. 1 is homogeneously mixed with 100 parts of polypropylene powder ("Propathene HF 20" of Messrs. ICI) and the mixture is re-granulated 5 times successively in a single screw extruder at a maximum temperature of 260°C and 100 r.p.m. The melt index (MI) of the material is measured after the 1st, 3rd and 5th extrusion respectively (2,160 g load at 230°C; figures in grams per 10 minutes). Degradation of the polymer manifests itself by a rapid increase of the melt index. An experiment was carried out in the same way in parallel, no stabiliser being added.

|  | Melt index | | | |
| --- | --- | --- | --- | --- |
|  | As received | 1st extrusion | 3rd extrusion | 5th extrusion |
| Unstabilised sample | 2.50 | 7.0 | 23.4 | 49.8 |
| Stabilised sample | 2.50 | 3.4 | 4.0 | 5.7 |

EXAMPLE 4

Stabilisation of polypropylene against degradation caused by light.

1,000 parts of polypropylene powder [melt index 20 (230°C, 2,160 g)] are mixed in a Brabender kneader at 200°C with 2 parts of β-(3,5-di-tert.butyl-4-hydroxyphenyl)-propionic acid octadecyl ester and 2.5 parts of Stabiliser No. 1. After homogenisation in this way, the mixture is taken from the kneader and is pre-formed by means of a toggle press into sheets 2-3 mm thick, which are subsequently converted at 260°C in a heated platen press, with the aid of suitable moulds, first into sheets 0.3 mm thick and, in a second operation, into sheets 0.1 mm thick.

The sheets prepared in this way are heat-treated at 150°C for 1 hour, cooling below 150°C being avoided, and, directly afterwards, are quenched in water at 15°C. The sheets prepared in this way exhibit a homogeneous structure with fine spherulites. Test pieces punched from them have an elongation of approx. 900%.

The polypropylene sheets prepared in this way are mounted on sample carriers and are exposed in an Xeno-150 testing apparatus. Pieces of sheet are taken out after varying times, five test pieces of each are punched and their elongation at break is determined. The time of exposure after which the elongation at break of the sheets has declined to 50% of its value before the exposure, is taken as a measure of the protective effect of the individual light protection agents. The values obtained are shown in the following table:

| Light protection agent | Hours of exposure in the Xeno apparatus until the tensile strength has fallen to 50% of its initial value |
|---|---|
| None, contains only 0.2 per cent | 800 |

| Light protection agent | Hours of exposure in the Xeno apparatus until the tensile strength has fallen to 50% of its initial value |
|---|---|
| by weight of β-(3,5-ditert.butyl-4-hydroxyphenyl)-propionic acid octadecyl ester 0.25 per cent by weight of N-(3,5-di-tert.butyl-4-hydroxybenzyl)-thiophosphoric acid O,O-diethyl ester hydrazide + 0.2 per cent by weight of β-(3,5-di-tert.butyl-4-hydroxyphenyl)-propionic acid octadecyl ester | 1,520 |

EXAMPLE 5

Stabilisation of mineral oil 0.2 g of Stabiliser No. 1 is dissolved in 50 ml of mineral oil (solvent refined paraffinic base oil HVI 65-LP509, Shell). The mixture is put into a glass-lined autoclave together with 5 ml of distilled water and a piece of highly purified copper wire. The autoclave is closed and the pressure is adjusted to 6.3 atmospheres gauge with oxygen. The whole autoclave is then dipped into an oil bath, previously heated to 150°C, and is rotated at 100 r.p.m., the axis of rotation making an angle of 30° to the horizontal. The maximum pressure value of approx. 13 atmospheres gauge is noted and the time is measured during which the pressure falls by 1.75 atmospheres gauge from its maximum value.

A test is carried out at the same time in which no stabiliser is added. The activity of the stabiliser manifests itself in a slower decrease of the pressure; that is to say a longer experimental time (= life).

| | Life |
|---|---|
| Unstabilised sample | 26 minutes |
| Stabilised sample | 168 minutes |

EXAMPLE 6

Stabilisation of polybutadiene rubber.

100 parts of polybutadiene ("Solprene 250" of Messrs. Phillips), previously stabilised with 0.36% of 2,6-ditert.butyl-p-cresol, are, in addition, kneaded for 30 minutes in a Brabender Plastograph at 150°C and 60 r.p.m. with 0.1 part of the stabiliser listed in the table which follows. During this time the resistance to kneading is continuously registered in the form of the torque. As a result of cross-linking occurring initially and subsequent degradation, there is a maximum in the torque value. The effectiveness of the stabilisers manifests itself in a reduction of the toruqe maximum.

Table

| Stabiliser No. | Torque maximum in grams × meters |
|---|---|
| Without stabiliser | 3,625 |
| 1 | 2,875 |

What we claim is:
1. Compounds of the formula

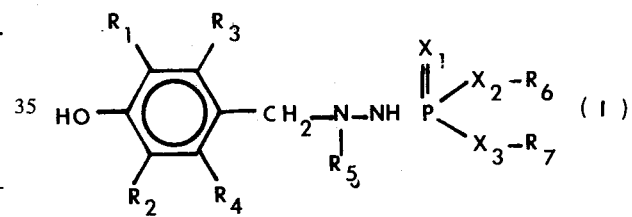

in which $R_1$ denotes alkyl having 1-8 carbon atoms, cycloalkyl having 6-8 carbon atoms, or aralkyl having 7-9 carbon atoms; $R_2$ denotes hydrogen, alkyl having 1-8 carbon atoms, cycloalkyl having 6-8 carbon atoms, or aralkyl having 7-9 carbon atoms, $R_3$ and $R_4$ independently of one another denote hydrogen or methyl, $R_5$ denotes hydrogen or one of the groups

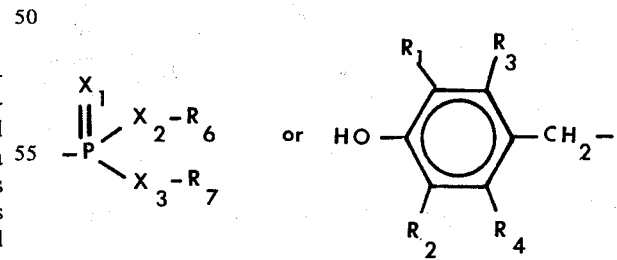

$R_6$ and $R_7$ independently of one another denote alkyl having 1-22 carbon atoms, cycloalkyl having 5-8 carbon atoms, halogenoalkyl having 2-18 carbon atoms, thiaalkyl having 3-21 carbon atoms, wherein $X_2$ and $X_3$ are linked to a carbon atom in the thiaalkyl radical which does not carry further heteroatoms, oxaalkyl having 3-21 carbon atoms, wherein $X_2$ and $X_3$ are linked to a carbon atom in the oxaalkyl radical which does not carry further hetero-atoms, alkenyl having 3–4 carbon atoms, aralkyl having 7–15 carbon atoms, phenyl, alkylphenyl having 7–14 carbon atoms, alkoxyphenyl having 7–14 carbon atoms, chlorophenyl or phenylphenyl, or $R_6$ and $R_7$ conjointly denote 1,2- or 1,3-alkylene having 2 to 8 carbon atoms, or o-phenylene, or, if $R_5$ denotes a phosphorus-free group, also a group

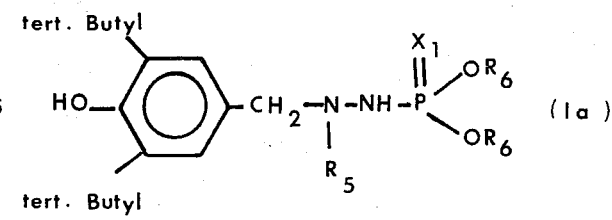

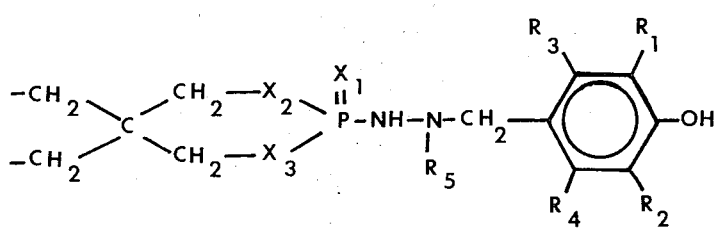

and $X_1$, $X_2$ and $X_3$ independently of one another denote oxygen and/or sulphur, not more than 2 radicals out of $X_1$, $X_2$ and $X_3$ being sulphur.

2. Compounds according to claim 1, of the formula I in which $R_1$ denotes alkyl having 1–4 carbon atoms, $R_2$ denotes alkyl having 3 or 4 carbon atoms, $R_3$ and $R_4$ denote hydrogen, $R_5$ denotes hydrogen or a group

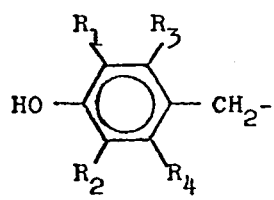

$R_6$ and $R_7$ independently of one another denote alkyl having 1–8 carbon atoms, benzyl, phenyl or alkylphenyl having 7–14 carbon atoms, or $R_6$ and $R_7$ conjointly denote ethylene, 1-methyltrimethylene, 2,2-dimethyltrimethylene, o-phenylene or a group

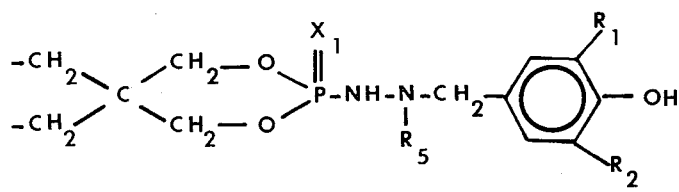

$X_1$ denotes oxygen or sulphur, and $X_2$ and $x_3$ denote oxygen.

3. Compounds according to claim 1, of the formula Ia in which $R_5$ denotes hydrogen or a group

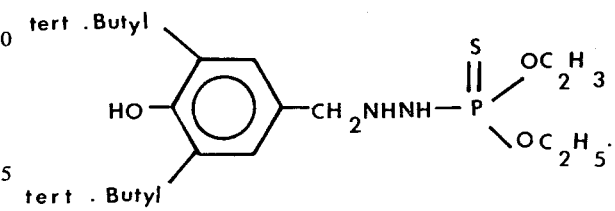

$R_6$ denotes alkyl having 1–8 carbon atoms, and $X_1$ denotes oxygen or sulphur.

4. Compound according to claim 1, of the formula

* * * * *